United States Patent [19]

Maki et al.

[11] Patent Number: 4,967,004

[45] Date of Patent: Oct. 30, 1990

[54] PROCESS FOR PRODUCING N,N-DIETHYLAMINOPHENOLS

[75] Inventors: Hiroshi Maki; Shigeru Sasaki, both of Chiba, Japan

[73] Assignee: Sumitomo Chemical Company, Limited, Osaka, Japan

[21] Appl. No.: 179,447

[22] Filed: Apr. 8, 1988

[30] Foreign Application Priority Data

Apr. 9, 1987 [JP] Japan .................................. 62-88068
Apr. 21, 1987 [JP] Japan .................................. 62-99047

[51] Int. Cl.$^5$ ............................................ C01C 209/00
[52] U.S. Cl. ................................. 564/397; 564/398; 564/437
[58] Field of Search ............... 564/397, 437, 398, 86, 564/177, 180, 184, 218; 260/508; 558/56; 560/43; 562/433

[56] References Cited

U.S. PATENT DOCUMENTS

4,760,183  7/1988  Papenfuhs et al. .................. 558/56

FOREIGN PATENT DOCUMENTS

1352826   2/1987  Fed. Rep. of Germany .
127337   10/1981  Japan .
1585018   2/1981  United Kingdom .

OTHER PUBLICATIONS

Chemical Abstracts, vol. 107, No. 13, Sep. 28, 1987, CA 115 359u.

Chemical Abstracts, vol. 85, No. 7, Aug. 16, 1979, CA 46 172r.

European Search Report EP 88303116.3.

*Primary Examiner*—Nathan M. Nutter
*Attorney, Agent, or Firm*—Sughrue, Mion, Zinn, Macpeak & Seas

[57] ABSTRACT

A process for producing an N,N-diethylaminophenol is disclosed, comprising subjecting an aminophenol to reductive alkylation with acetaldehyde in the presence of a solvent, a catalyst, and hydrogen is disclosed, in which the reaction mixture from which the catalyst has been removed is subjected to distillation while maintaining the temperature of the bottom at 160° C. or lower to substantially remove the unreacted acetaldehyde and the solvent, the residual bottom is distilled while maintaining the temperature of the bottom at 200° C. or lower to recover a crude N,N-diethylaminophenol as a distillate, and the recovered crude N,N-diethylaminophenol is contacted with a solvent to which at least one of acid sulfites and dithionites has been added, said solvent being substantially incompatible with the N,N-diethylaminophenol, in an inert gas atmosphere, followed by precipitating and recovering the N,N-diethylaminophenol by cooling. N,N-Diethylaminophenols of high purity can be obtained in high yield without involving problems, such as production of large quantities of waste water and sludge, corrosion of materials, and coloring with time.

4 Claims, No Drawings

PROCESS FOR PRODUCING N,N-DIETHYLAMINOPHENOLS

FIELD OF THE INVENTION

This invention relates to a process for producing an N,N-diethylaminophenol. N,N-Diethylaminophenols are of high industrial importance as intermediates for the production of dyes for heat-sensitive or pressure-sensitive paper, xanthene dyes, fluorescent dyes, etc.

BACKGROUND OF THE INVENTION

Conventionally known processes for synthesizing N,N-diethylaminophenols include (1) a method comprising obtaining sodium metanilate from nitrobenzene ethylating sodium metanilate with ethyl chloride or diethyl sulfate, and subjecting the ethylated compound to alkali fusion, (2) a method comprising reacting a dihydric phenol with diethylamine in the presence of an acid catalyst, and (3) a method comprising ethylating an aminophenol with ethyl chloride or diethyl sulfate in the presence of an alkali salt.

The method (1) is called an alkali fusion process. This method is of little industrial interest because it produces large quantities of waste water and sludge and also requires a lengthy process.

The method (2), in which the reaction is carried out using an excessive amount of diethylamine in the presence of an acid catalyst at a high temperature and a high pressure, provides N,N-diethylaminophenols only in a low yield with large amounts of by-products, and the excess diethylamine should be recovered. There is a further problem of corrosion of materials. Therefore, this method is very difficult to carry out on an industrial scale.

The method (3), though using an alkali salt as an acid scavenger, still involves a problem of material corrosion. Further, it is difficult to separate a by-product chloride and a produced N,N-diethylaminophenol after completion of the reaction, and purification of the desired product produces a large quantity of waste water, thus making the process considerably complicated.

In addition, while any of the methods (1), (2), and (3) inevitably requires neutralization treatment with an acid or an alkali for recovery of the produced N,N-diethylaminophenol, it is difficult, by nature of amino group-containing compounds, to judge the end point of neutralization. Moreover, the thermal instability of the N,N-diethylaminophenols has permitted of no use of distillation for purification. This naturally limits the quality of the finally obtained N,N-diethylaminophenol. More specifically, the N,N-diethylaminophenols produced by these conventional methods generally assume brown due to a small tar content (heavy content), which has often adversely affected their commercial value.

It has also been proposed that an aminophenol is subjected to reductive alkylation with acetaldehyde and the produced N,N-diethylaminophenol is recovered by distillation. The product obtained by this technique has markedly improved quality over those obtained by the methods (1) to (3). Nevertheless, the product is still unsatisfactory in quality, particularly considering that the demand of N,N-diethylaminophenols for the production of dyes for heat-sensitive or pressure-sensitive paper has recently been increasing. Thus, it has been keenly demanded to develop N,N-diethylaminophenols having higher purity and suffering from lesser coloring, depending on the end use.

SUMMARY OF THE INVENTION

Accordingly, one object of this invention is to provide a process for producing an N,N-diethylaminophenol of high quality in a high yield without involving the above-described problems associated with the conventional techniques, such as production of large quantities of waste water and sludge, corrosion of materials, and the like.

That is, the present invention relates to an improved process for producing an N,N-diethylaminophenol comprising subjecting an aminophenol to reductive alkylation with acetaldehyde in the presence of a solvent, a catalyst, and hydrogen, in which the reaction mixture from which the catalyst has been removed is subjected to distillation while maintaining the temperature of the bottom at 160° C. or lower to substantially remove the unreacted acetaldehyde and the solvent, the residual bottom is distilled while maintaining the temperature of the bottom at 200° C. or lower to recover a crude N,N-diethylaminophenol diethylaminophenol as a distillate, and the recovered crude N,N-diethylaminophenol is contacted with a solvent to which at least one of acid sulfites and dithionites has been added, said solvent being substantially incompatible with the N,N-diethylaminophenol, in an inert gas atmosphere, followed by precipitating and recovering the N,N-diethylaminophenol by cooling.

DETAILED DESCRIPTION OF THE INVENTION

The aminophenols which can be used in the present invention include o-aminophenol, m-aminophenol, p-aminophenol, etc., with m-aminophenol being particularly preferred. The N,N-diethylaminophenols specifically include N,N-diethyl-o-aminophenol, N,N-diethyl-m-aminophenol, N,N-diethyl-p-aminophenol, etc., with N,N-diethyl-m-aminophenol being particularly preferred.

The reductive alkylation according to the present invention can be carried out easily in a known manner, that is an aminophenol, a solvent, and a catalyst are charged in a reactor, and acetaldehyde is then continuously fed thereinto while applying a hydrogen pressure. The solvent to be generally used includes aliphatic alcohols, e.g., methanol, ethanol, propanol, etc., and the catalyst includes those capable of catalyzing reductive alkylation, such as platinum, palladium, nickel, etc.

The acetaldehyde is usually used in an amount of from 2.1 to 4 mols per mol of the aminophenol. The solvent is used in an amount of from 1 to 20 parts by weight per part by weight of the aminophenol. The amount of the catalyst to be used ranges from 0.005 to 0.1 part by weight per part by weight of the aminophenol.

The reaction temperature is from room temperature to 150° C. The hydrogen pressure is not particularly limited and is usually 20 kg/cm$^2$G or less.

After the reductive alkylation, the catalyst is removed from the reaction mixture, for example, by filtration. The reaction mixture is then distilled while maintaining the bottom temperature at 160° C. or lower to thereby substantially remove the unreacted acetaldehyde and the solvent while recovering the N,N-diethylaminophenol-containing bottom. The resulting bottom containing virtually no acetaldehyde or solvent is further distilled while maintaining the bottom temperature at 200° C. or lower to recover a crude N,N-diethylaminophenol as a distillate.

The process of the present invention is characterized in that the thus obtained crude N,N-diethylaminophenol is contacted with a solvent which is substantially incompatible with the N,N-diethylaminophenol and contains one or more of acid sulfites and dithionites in an inert gas atmosphere, and the resulting mixture is then cooled to precipitate the N,N-diethylaminophenol for recovery.

The solvent which is substantially incompatible with N,N-diethylaminophenols includes water and aliphatic hydrocarbons. Preferred examples of the aliphatic hydrocarbons are hexane, heptane, octane, and cyclohexane. The solvent is usually used in an amount of from 1 to 10 parts by weight per part by weight of the crude N,N-diethylaminophenol. The inert gas suitably includes nitrogen, argon, and helium.

Examples of the acid sulfites which can be used in the present invention are acid sodium sulfite and acid potassium sulfite. Examples of the dithionites are sodium dithionite and potassium dithionite. The acid sulfites and/or dithionites are added to the solvent in a total amount of from 0.1 to 10 parts by weight, preferably from 0.5 to 7.5 parts weight, per 100 parts by weight of the crude N,N-diethylaminophenol. If the amount of these additives is less than 0.1 part, the finally obtained product cannot be sufficiently prevented from coloring with time. If it exceeds 10 parts, the additives remain in the final product in an excessive amount, causing deterioration of product quality.

The mode of addition of the acid sulfite or dithionite is not particularly restricted. For example, they may be added in the form of a powder or a liquid, e.g., an aqueous solution. The above-enumerated acid sulfite and dithionite may be used either individually or in combination of two or more thereof.

The contact between the crude N,N-diethylaminophenol and the solvent containing an acid sulfite or a dithionite can be effected usually by adding the crude N,N-diethylaminophenol in a molten state as recovered by distillation to the solvent having been previously placed in an inert gas atmosphere while stirring. At the time of addition, the solvent may be kept at the temperature where N,N-diethylaminophenols are melted or either higher or lower than that. From the standpoint of removal of impurities, it is preferable that the temperature after addition of the crude N,N-diethylaminophenol should be kept at a temperature no less than the temperature where the crude N,N-diethylaminophenol is melted. The temperature where the crude N,N-diethylaminophenol is melted is usually 50° C. or higher, though varing depending on the amounts of impurities contained in the crude N,N-diethylaminophenol, the ratio of the crude N,N-diethylaminophenol to the solvent, and the like.

The contact between the crude N,N-diethylaminophenol and the solvent can be carried out either in a batch system or in a continuous system. After the contact therebetween under stirring, the mixture is cooled in a usual manner to crystallize and precipitiate the N,N-diethylaminophenol. In order to assure smooth crystallization, it is preferable to add seed crystals to the system.

The precipitated N,N-diethylaminophenol is recovered by usual filtration operations, such as filtration under reduced pressure or under elevated pressure or by centrifugation. If desired, the filter cake may be subjected to rinse washing or repulp washing with water having dissolved therein an acid sulfite and/or a dithionite. The thus collected cake of the N,N-diethylaminophenol is further worked-up, for example, by drying to obtain a final product.

According to the present invention, N,N-diethylaminophenols can be obtained in good yield as a pale yellowish white or pale red solid without encountering various problems associated with the conventional techniques. Besides, the products obtained retain their quality for a prolonged period of time, being prevented from coloring with the passage of time.

The present invention is now illustrated in greater detail with reference to Examples and Comparative Example, but it should be understood that the present invention is not deemed to be limited thereto. In these examples, all the percents are by weight unless otherwise indicated.

The N,N-diethylaminophenols prepared in the examples were evaluated for coloring with time in accordance with the following test method.

The sample was put in a plastic container and allowed to stand in air at room temperature in a dark place for a prescribed period of time. The sample (1.5 g) was then dissolved in 5 ml of hydrochloric acid, and isopropyl alcohol was added to the solution to make 100 ml. The solution was placed in a 10 mm quartz cell, and the absorbance at a wavelength of 570 nm was measured by means of a spectrophotometer manufactured by Hitachi, Ltd. The degree of coloring was determined by calculating a molar extinction coefficient from the measured absorbance according to equation:

$$\text{Molar Extinction Coefficient} = \frac{(\text{Absorbance}) \times 100}{\frac{W}{165.2} \times 1000 \times \frac{(\text{Purity of Product})}{100}}$$

In the above equation, W is a weight (g) of the sample; the value "165.2" is a molecular weight of N,N-diethyl-m-aminophenol; and the purity of product is a diazo value purity (%).

For better understanding, rough correspondence of the molar extinction coefficient to appearance by visual observation is shown below.

Up to 0.4: Pale yellowish white to faintly pale red
0.4 to 1.0: Faintly pale red to pale brown
1.0 and more: pale brown to blacky brown, inclusive of brown Molar extinction coefficients up to and including 1.0, which correspond to a pale browish appearance, meet the purpose of the present invention.

EXAMPLE 1

1) Preparation of Crude N,N-Diethyl-m-Aminophenol

In a 5 l-volume SUS-made autoclave equipped with a stirrer were charged 163.7 g (1.5 mols) of m-aminophenol, 1814 g of methanol, and 4.1 g of 5% platinum-on-carbon. To the mixture was continuously fed 165.2 g (3.75 mols) of acetaldehyde at 40° C. under a constant hydrogen pressure of 10 kg/cm$^2$G over a period of 5 hours to effect reductive alkylation. After completion of the continuous addition of acetaldehyde, the mixture was maintained at that temperature for an additional 20 minutes, followed by cooling. The catalyst was removed from the reaction mixture by filtration.

The reaction mixture was continuously fed to an egg-plant flask on an oil bath over a period of 3 hours to effect distillation under reduced pressure to thereby remove the unreacted aldehyde and methanol. After the end of the feeding, the system was batchwise concentrated to substantially remove the aldehyde and methanol. The operation was carried out at a constant pressure of 300 mmHg and at a bottom temperature of 120° C. or lower. When the bottom temperature reached 120° C., the distillation was stopped.

Subsequently, the resulting bottom was batchwise distilled under reduced pressure controlled at 3 mmHg to recover the crude N,N-diethyl-m-aminophenol. The distillation was stopped when the bottom temperature reached 170° C. The resulting liquid crude N,N-diethyl-m-aminophenol was subjected to the next purification step.

2) Purification of Crude N,N-Diethyl-m-Aminophenol

In a 1 l-volume separable flask equipped with a stirrer, a baffle, a thermometer, and a condenser was charged 400 g of water in a nitrogen atmosphere, and 2.5 g of sodium dithionite was then added thereto, followed by heating the mixture to 50° C. To the mixture maintained at 50° C. was added 100 g of the crude N,N-diethyl-m-aminophenol, and the inner temperature was raised up to 65° C. After confirming melting of the N,N-diethyl-m-aminophenol, cooling of the mixture was started while stirring. When the inner temperature was dropped to 60° C, 0.1 g of seed crystals of N,N-diethyl-m-aminophenol was added. The N,N-diethyl-m-aminophenol began to precipitate at around 57° C. Cooling was continued at a rate of about 0.2 to 0.3° C./min to drop the temperature to 30° C., where crystallization completed. The cake of N,N-diethyl-m-aminophenol was collected by filtration under reduced pressure.

The resulting cake was dried at 40° C./30 mmHg for 2 hours to obtain 98.4 g of N,N-diethyl-m-aminophenol as granules having a pale yellowish white appearance. The product was found to have a purity of 99.8% as determined by gas chromatography and to have no tar content as determined by gel permeation chromatography.

Coloring with lapsing at room temperature in a dark place in air was evaluated according to the above-described test method. As a result, the molar extinction coefficient of the sample having been preserved for 2 months was 0.5, namely the sample had a faintly pale red appearance, indicating satisfactory quality of the product in view of the fact that the sample immediately after the preparation has a molar extinction coefficient of 0.1.

EXAMPLES 2 TO 6 AND COMPARATIVE EXAMPLE 1

The same procedure of Example 1 was repeated, except for changing the kind and amount of the compound added to the purification system as shown in Table 1 below. Each of the resulting products was evaluated for coloring with lapsing in the same manner as in Example 1, and the results obtained are also shown in Table 1.

TABLE 1

| | Compound Added | Amount Added (g*) | Molar Extinction Coefficient | | |
|---|---|---|---|---|---|
| | | | After 0 Mth. | After 1 Mth. | After 2 Mths. |
| Example No. | | | | | |
| 2 | Sodium dithionite | 5.0 | 0.1 | 0.2 | 0.4 |
| 3 | Sodium dithionite | 1.0 | 0.1 | 0.4 | 0.7 |
| 4 | Potassium dithionite | 2.5 | 0.1 | 0.3 | 0.5 |
| 5 | Acid sodium sulfite | 2.5 | 0.1 | 0.3 | 0.6 |
| 6 | Acid potassium sulfite | 2.5 | 0.1 | 0.3 | 0.6 |
| Comparative Example 1 | none | — | 0.1 | 1.5 | 7.4 |

Note:
*Weight per 100 g of the crude N,N-diethyl-m-aminophenol.

As is apparent from Table 1, the products obtained in Examples 2 to 6 had a very satisfactory appearance of faintly pale red to faintly pale brown, whereas the product of Comparative Example 1 changed its color with lapsing to blacky brown.

The present invention achieves great developments in settlement of the problems associated with the conventional methods, such as corrosion of materials, production of large quantities of waste water and sludge, coloring of the product, and the like, and establishes a process for producing N,N-diethylaminophenols with high industrial advantages.

While the invention has been described in detail and with reference to specific embodiments thereof, it will be apparent to one skilled in the art that various changes and modifications can be made therein without departing from the spirit and scope thereof.

What is claimed is:

1. A process for producing an N,N-diethylaminophenol comprising the steps of:
   subjecting an aminophenol to reductive alkylation with acetaldehyde in the presence of a first solvent, a catalyst, and hydrogen to form a reductive alkylation reaction mixture;
   removing said first catalyst from said reductive alkylation reaction mixture;
   distilling the resulting reaction mixture in a distillation column while maintaining the bottom temperature of the distillation column at 160° C. or lower to substantially remove the unreacted acetaldehyde and said first solvent;
   distilling the residue of said distilled reaction mixture while maintaining the bottom temperature of said distillation column at 200° C. or lower to recover crude N,N-diethylaminophenol as a distillate;
   contacting said recovered crude N,N-diethylaminophenol distillate with a second solvent in an inert gas atmosphere composed of at least one gas selected from a group consisting of nitrogen, argon, and helium, to form a solution; said second solvent comprising
   i) at least one component selected from a group consisting of water and aliphatic hydrocarbons, and
   ii) at least one component selected from a group consisting of acid sulfites and dithionites;

cooling the solution containing said crude N,N-diethylaminophenol and said second solvent to precipitate substantially pure N,N-diethylaminophenol; and recovering said N,N-diethylaminophenol.

2. A process as claimed in claim 1, wherein said acid sulfites are acid sodium sulfite and acid potassium sulfite, and said dithionites are sodium dithionite and potassium dithionite.

3. A process as claimed in claim 1, wherein said acid sulfites and/or dithionites are added in a total amount of from 0.1 to 10 parts by weight per 100 parts by weight of the crude N,N-diethylaminophenol.

4. A process as claimed in claim 1, wherein said aminophenol is m-aminophenol, and said N,N-diethylaminophenol is N,N-diethyl-m-aminophenol.

* * * * *